United States Patent [19]

Singh

[11] Patent Number: 4,461,639
[45] Date of Patent: Jul. 24, 1984

[54] N-HALO PHOSPHONOMETHYLAMINE DERIVATIVES AS HERBICIDES

[75] Inventor: Rajendra K. Singh, Maryland Heights, Mo.

[73] Assignee: Monsanto Company, St. Louis, Mo.

[21] Appl. No.: 443,276

[22] Filed: Nov. 22, 1982

[51] Int. Cl.$^3$ .................. A01N 57/22; C07F 9/40
[52] U.S. Cl. ................................ 71/86; 260/940
[58] Field of Search .................... 260/940; 71/86

[56] References Cited
U.S. PATENT DOCUMENTS

| | | | |
|---|---|---|---|
| 4,008,296 | 2/1977 | Barton | 260/940 |
| 4,252,554 | 2/1981 | Dutra et al. | 71/87 |
| 4,300,943 | 11/1981 | Dutra et al. | 71/87 |
| 4,322,238 | 3/1982 | Dutra et al. | 71/86 |

Primary Examiner—Anton H. Sutto
Attorney, Agent, or Firm—David Bennett; Richard H. Shear; Arnold H. Cole

[57] ABSTRACT

N-halo, N-cyanomethyl, diaryloxyphosphinylmethylamine compounds are described. These compounds have herbicidal activity and are useful active ingredients in herbicidal formulations.

10 Claims, No Drawings

N-HALO PHOSPHONOMETHYLAMINE DERIVATIVES AS HERBICIDES

BACKGROUND OF THE INVENTION

This invention relates to certain novel N-halo phosphonomethylamine derivatives. These novel compounds are of interest because they demonstrate activity as non-selective systemic herbicides.

DESCRIPTION OF THE INVENTION

The novel compounds of the invention have the formula:

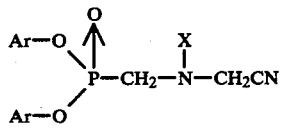

wherein X is selected from chlorine and bromine, and each Ar is selected from the group consisting of substituted and unsubstituted aryl radicals in which the substituents are selected from $C_1$ to $C_4$ alkyl, $C_1$ to $C_3$ alkoxy and halogen groups.

In general the preferred halogen substituent on the nitrogen atom is chlorine. The preferred Ar group is unsubstituted phenyl but other possible Ar groups include naphthyl; p-methoxy-phenyl; 4-methyl-phenyl; 2-chlorophenyl; 3-methyl, 4-chloro, phenyl; and 2-chloro-4-methoxy-phenyl.

Preferred compounds of the invention have identical Ar groups and, as indicated above, the most preferred compounds are the diphenyl derivatives.

Representative compounds according to the invention include: the diphenyl ester of [chloro(cyanomethyl)amino] methyl phosphonic acid; the bis(4-methoxy phenyl) ester of [chloro(cyanomethyl)amino] methyl phosphonic acid; the bis(4-chloro,3-methyl-phenyl) ester of [chloro(cyanomethyl)amino] methyl phosphonic acid; the bis-(2-naphthalenyl) ester of [chloro(-cyanomethyl) amino] methyl phosphonic acid; and the same esters of [bromo(cyanomethyl)-amino] methyl-phosphonic acid.

The compounds of the invention can be obtained by reaction of a compound having the formula:

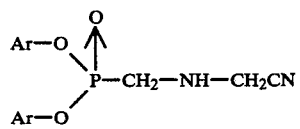

with a halogen source such as N-nalosuccinimide. This reaction which may be rather slow can take several days. It is conveniently conducted in a non-polar solvent such as diethyl ether with continued agitation at room temperature.

The above compound (I) may be obtained by neutralization of a corresponding acid salt using an alkali. The neutralization is preferably conducted at low temperatures around 0° C. and in an organic solvent such as dichloromethane. The acid salt itself may be obtained by any of the techniques described in U.S. Pat. No. 4,067,719 which is incorporated herein by reference.

DESCRIPTION OF PREFERRED EMBODIMENTS

The invention is now more particularly described with reference to the following examples which are for the purposes of illustration only and are intended to imply no essential limitation or restriction on the scope of the invention.

EXAMPLE 1

This example describes the preparation of a compound having the formula:

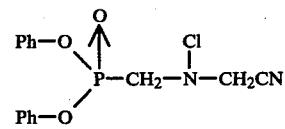

A reaction mixture comprising 3.02 gm of the diphenyl ester of (cyanomethylamino)methyl phosphonic acid (freshly prepared from the methyl sulfonic acid salt by neutralization at 0° C. using an alkali), and 1.6 gm of N-chlorosuccinimide in 200 ml of diethyl ether was stirred for 12 days at ambient temperatures. The reaction mixture was then filtered through celite (clay) and the ether solvent was evaporated leaving 3.8 gm of product. The product was purified by placing it on a column of about 70 gm of silica gel and eluting with a 60:40 mixture of cyclohexane and ethyl acetate. The purified product weighed 2.4 gm.

EXAMPLE 2

This example describes the production of a compound having the formula:

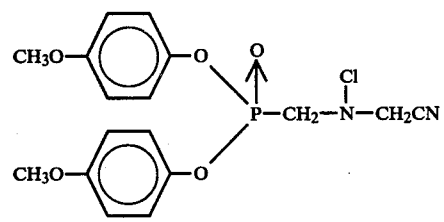

A reaction mixture comprising 11.4 gm of the bis(4-methoxyphenyl) ester of (cyanomethylamino)methyl phosphonic acid, 6.3 gm of N-chlorosuccinimide and 400 ml of diethyl ether was stirred for 3 days at room temperature. After that time, the mixture was yellow and a gummy yellow substance had been deposited on the sides of the flask. The mixture was filtered under suction to remove the solid and a further 6.3 gm of N-chlorosuccinimide were added and stirring at room temperature was recommenced. Six days later a $^{31}P$ nuclear magnetic resonance analysis showed that reaction was complete.

The reaction mixture was concentrated to half volume and filtered through celite to give 200 ml of product in solution. One-third of this was concentrated in vacuo and then purified chromatographically on 60 gm of silica gel using first, 500 ml of a 20:80 ethyl acetate/cyclohexane mixture and then a 40:60 ethyl acetate/cyclohexane mixture. A pure product (0.6 gm) was isolated and its structure confirmed by proton and $^{31}P$ nuclear magnetic resonance spectroscopy.

EXAMPLE 3

This example describes the production of a compound having the formula:

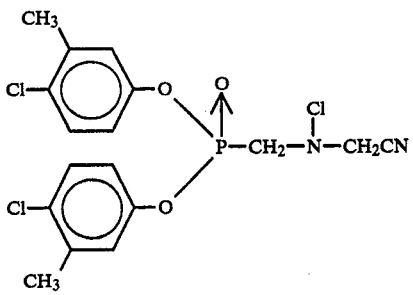

A reaction mixture comprising 8.4 gm of the bis(4-chloro-3-methyl phenyl) ester of (cyanomethylamino)methyl phosphonic acid (freshly prepared from the corresponding methylsulfonic acid salt by neutralization at 0° C. using an alkali), 3.42 gm of N-chlorosuccinimide and 400 ml of diethyl ether was stirred for 11 days at ambient temperatures. Analysis of the reaction mixture using $^{31}$P nuclear magnetic resonance spectroscopy showed that the reaction was in fact complete. The solution was concentrated in vacuo at 28° C. to about half volume and then filtered through clay to give a clear yellow solution which was further concentrated in vacuo. About 70 ml of the concentrated solution was separated chromatographically on 41 gm of silica gel using a 20:80 ethyl acetate/cyclohexane mixture.

Structure of the pure product was confirmed by proton and $^{31}$P nuclear magnetic resonance spectroscopy.

EXAMPLE 4

This example describes the preparation of a compound having the formula:

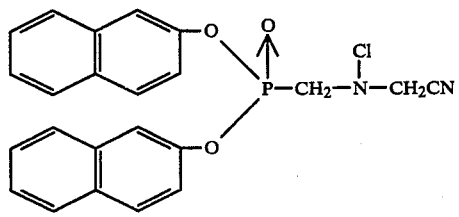

A reaction mixture comprising 8.0 gm of the bis(2-naphthalenyl) ester of (cyanomethylamino)methyl phosphonic acid (freshly prepared from the corresponding methyl sulfonic acid salt by neutralization at 0° C. using alkali), and 5.3 gm of N-chlorosuccinimide in 800 ml of diethyl ether. The mixture was stirred at room temperature for 15 days after which it was filtered through celite and reduced to ¼ volume under vacuum. Analysis using $^{31}$P nuclear magnetic resonance spectroscopy showed the reaction was complete.

About 8 gm of the product were chromatographed over 75 gm of silica gel using 400 ml of 20:80 ethyl acetate/cyclohexane mixture followed by 400 ml of a 40:60 mixture of the same solvents. A purified product (1.2 gm) was obtained that proved to have limited stability.

The products obtained from Examples 1 to 4 had limited aqueous solubility and were submitted for evaluation as herbicides as a 1% solution in tetrahydrofuran.

EXAMPLE 5

This example illustrates the post-emergent herbicidal activity of the compounds prepared as described in Examples 1–4.

A 1.0% solution in tetrahydrofuran of each compound was formulated directly before application into a spray solution comprising 3 parts of cyclohexanone and 1 part of a surfactant. The surfactant was formed of 35 parts of the butylamine salt of dodecylbenzylsulfonic acid and 65 parts of tall oil condensed with ethylene oxide in the ratio of 11 moles of ethylene oxide to 1 mole of tall oil.

The spray was applied to two-week-old plants of the indicated species in amounts sufficient to give the indicated application rates. The plants were then placed in a greenhouse and left under good growing conditions for four weeks. The condition of the plants was observed after two and four weeks and a determination made of the extent to which they had been injured. This was translated to a code as follows:

| | |
|---|---|
| 0–24% injured | 0 |
| 25–49% injured | 1 |
| 50–74% injured | 2 |
| 75–99% injured | 3 |
| 100% killed | 4 |

The plants treated and the code letter assigned to them were as follows:

| | |
|---|---|
| A - Canada Thistle | K - Barnyardgrass |
| B - Cocklebur | L - Soybean |
| C - Velvetleaf | M - Sugar Beet |
| D - Morning Glory | N - Wheat |
| E - Lambsquarters | O - Rice |
| F - Pa. Smartweed | P - Sorghum |
| G - Yellow Nutsedge | Q - Wild Buckwheat |
| H - Quackgrass | R - Hemp Sesbania |
| I - Johnsongrass | S - Proso Millet |
| J - Downy Brome | T - Crabgrass |

The response of the plants to the treatment is set forth on Table 1.

TABLE 1

POST-EMERGENT HERBICIDAL RESPONSE

| Compound | Application Level kg/h | WAT* | A | B | C | D | E | F | G | H | I | J | K | L | M | N | O | P | Q | R | S | T |
|---|---|---|---|---|---|---|---|---|---|---|---|---|---|---|---|---|---|---|---|---|---|---|
| Ex. 1 | 11.2 | 2 | 1 | 3 | 2 | 1 | 3 | 2 | 1 | 1 | 3 | 1 | 3 | | | | | | | | | |
| | 11.2 | 4 | 1 | 3 | 3 | 2 | 4 | 3 | 0 | 1 | 2 | 2 | 3 | — | — | — | — | — | — | — | — | — |
| | 5.6 | 2 | 1 | 3 | 1 | 1 | 3 | 1 | 2 | 1 | 3 | 0 | 3 | | | | | | | | | |
| | 5.6 | 4 | 2 | 4 | 1 | 2 | 3 | 4 | 4 | 1 | 3 | 0 | 3 | — | — | — | — | — | — | — | — | — |
| | 5.6 | 2 | — | 3 | 2 | 3 | 3 | 3 | — | — | — | 3 | 3 | 2 | 2 | 2 | 3 | 3 | 2 | 1 | 3 | — |
| | 5.6 | 4 | — | 3 | 3 | 3 | 3 | 4 | — | — | — | 3 | 4 | 3 | 2 | 3 | 3 | 4 | 3 | 1 | 3 | — |
| | 1.2 | 2 | — | 1 | 1 | 1 | 2 | 2 | — | — | — | 1 | 2 | 1 | 1 | 1 | 1 | 2 | 1 | — | 1 | — |

TABLE 1-continued
POST-EMERGENT HERBICIDAL RESPONSE

| Compound | Application Level kg/h | WAT* | A | B | C | D | E | F | G | H | I | J | K | L | M | N | O | P | Q | R | S | T |
|---|---|---|---|---|---|---|---|---|---|---|---|---|---|---|---|---|---|---|---|---|---|---|
| | 1.2 | 4 | — | 2 | 0 | 1 | 1 | 1 | — | — | — | 0 | 2 | 2 | 0 | 1 | 1 | 3 | 1 | 0 | 1 | — |
| Ex. 2 | 11.2 | 2 | 2 | 3 | 1 | 3 | 3 | 1 | 2 | 1 | 1 | 1 | 2 | — | — | — | — | — | — | — | — | — |
| | 11.2 | 4 | 2 | 2 | 2 | 3 | 3 | 0 | 2 | 1 | 0 | 2 | 2 | — | — | — | — | — | — | — | — | — |
| | 5.6 | 2 | 1 | 2 | 2 | 2 | 3 | 1 | 2 | 1 | 1 | 1 | 2 | — | — | — | — | — | — | — | — | — |
| | 5.6 | 4 | 2 | 2 | 3 | 2 | 3 | 1 | 2 | 1 | 1 | 1 | 2 | — | — | — | — | — | — | — | — | — |
| | 5.6 | 2 | — | 2 | 2 | 3 | 3 | 4 | — | — | — | 1 | 1 | 2 | 1 | 2 | 1 | 2 | 2 | 1 | 1 | 3 |
| | 5.6 | 4 | — | 3 | 2 | 2 | 3 | 4 | — | — | — | 1 | 1 | 2 | 0 | 2 | 1 | 2 | 2 | 1 | 1 | 3 |
| | 1.2 | 2 | — | 2 | 2 | 2 | 3 | 2 | — | — | — | 1 | 0 | 1 | 1 | 2 | 1 | 2 | 1 | 0 | 0 | 3 |
| | 1.2 | 4 | — | 2 | 2 | 1 | 3 | 2 | — | — | — | 1 | 0 | 1 | 0 | 1 | 1 | 3 | 1 | 0 | 1 | 3 |
| Ex. 3 | 5.6 | 2 | 0 | 2 | 1 | 2 | 4 | 2 | 1 | 0 | 0 | 0 | 2 | — | — | — | — | — | — | — | — | — |
| | 5.6 | 4 | 0 | 2 | 2 | 2 | 4 | 2 | 1 | 0 | 0 | 0 | 2 | — | — | — | — | — | — | — | — | — |
| | 5.6 | 2 | — | 3 | 2 | 3 | 4 | 2 | — | — | — | 2 | 2 | 1 | 1 | 1 | 1 | 3 | 2 | 1 | 1 | 3 |
| | 5.6 | 4 | — | 3 | 2 | 3 | 4 | 2 | — | — | — | 2 | 3 | 1 | 1 | 0 | 2 | 4 | 3 | 1 | 2 | 3 |
| Ex. 4 | 5.6 | 2 | — | 1 | 0 | 0 | 3 | 2 | 0 | 0 | 0 | 0 | 1 | — | — | — | — | — | — | — | — | — |
| | 5.6 | 4 | — | 2 | 0 | 2 | 1 | 1 | — | — | — | 0 | 1 | 1 | 1 | — | 1 | 2 | 2 | 0 | 0 | 2 |

*WAT = Weeks After Treatment

As can be seen from the data in Table 1, as the degree of complexity of the aryl group increases, there is an apparent reduction in herbicidal efficacy.

The herbicidal compositions, including concentrates which require dilution prior to application to the plants, of this invention contain from 5 to 95 parts by weight of at least one compound of this invention and from 5 to 95 parts by weight of an adjuvant in liquid or solid form; for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers, and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent," it is understood that wetting agents, dispersing agents, suspending agents, and emulsifying agents are included therein. Anionic, cationic, and non-ionic agents can be used with equal facility.

Preferred wetting agents are alkyl benzene and alkyl naphthalene sulfonates, sulfated fatty alcohols, amines or acid amides, long-chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate, and sodium N-methyl-N-(long-chain acid) laurates.

When operating in accordance with the present invention, effective amounts of the compound or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers, and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compound or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes, and modifications may be resorted to without departing from the spirit

What is claimed is:

1. A compound having the formula:

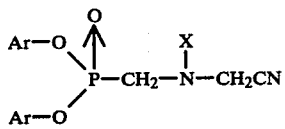

wherein X is selected from the group consisting of bromine and chlorine; and Ar groups are each individually selected from the group consisting of mono- and di-substituted and unsubstituted aryl groups in which the substituents are selected from $C_1$ to $C_4$ alkyl, $C_1$ to $C_3$ alkoxy and halogen groups.

2. A compound according to claim 1 in which X represents chlorine.

3. A compound according to claim 2 in which each Ar group is selected from substituted and unsubstituted phenyl groups wherein the substituents are selected from the group consisting of chlorine, methyl and methoxy.

4. The diphenyl ester of [chloro(cyanomethyl) amino]-methyl phosphonic acid.

5. A herbicidal composition comprising from 5 to 95 parts by weight of a compound according to claim 1 an from 95 to 5 parts by weight of an adjuvant.

6. A herbicidal composition comprising from 5 to 95 parts by weight of a compound according to claim 3 and from 95 to 5 parts by weight of an adjuvant.

7. A herbicidal composition comprising from 5 to 95 parts by weight of a compound according to claim 4 and from 95 to 5 parts by weight of an adjuvant.

8. A herbicidal process which comprises applying to a plant a herbicidally effective amount of a composition according to claim 5.

9. A herbicidal process which comprises applying to a plant a herbicidally effective amount of a composition according to claim 6.

10. A herbicidal process which comprises applying to a plant a herbicidally effective amount of a composition according to claim 7.

* * * * *